(12) United States Patent
Richard

(10) Patent No.: US 9,987,221 B2
(45) Date of Patent: Jun. 5, 2018

(54) INJECTABLE HYDROGEL COMPOSITIONS

(75) Inventor: Robert E. Richard, Wrentham, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 2107 days.

(21) Appl. No.: 12/195,806

(22) Filed: Aug. 21, 2008

(65) Prior Publication Data

US 2009/0053276 A1 Feb. 26, 2009

Related U.S. Application Data

(60) Provisional application No. 60/965,930, filed on Aug. 23, 2007.

(51) Int. Cl.
*A61K 9/00* (2006.01)
*A61K 9/16* (2006.01)
*A61K 9/10* (2006.01)

(52) U.S. Cl.
CPC .............. *A61K 9/0019* (2013.01); *A61K 9/10* (2013.01); *A61K 9/1635* (2013.01)

(58) Field of Classification Search
None
See application file for complete search history.

(56) References Cited

U.S. PATENT DOCUMENTS

| | | | | |
|---|---|---|---|---|
| 5,149,543 | A * | 9/1992 | Cohen et al. | 424/499 |
| 5,342,395 | A * | 8/1994 | Jarrett et al. | 606/219 |
| 5,840,338 | A * | 11/1998 | Roos et al. | 424/488 |
| 5,876,741 | A * | 3/1999 | Ron | 424/423 |
| 6,495,164 | B1 * | 12/2002 | Ramstack et al. | 424/489 |
| 6,610,841 | B1 * | 8/2003 | Warren | 536/25.3 |
| 2001/0046518 | A1 * | 11/2001 | Sawhney | 424/486 |
| 2003/0156618 | A1 * | 8/2003 | Ohnishi et al. | 374/43 |
| 2003/0206864 | A1 | 11/2003 | Mangin | |
| 2003/0211165 | A1 * | 11/2003 | Vogel et al. | 424/493 |
| 2004/0096508 | A1 | 5/2004 | Gutowska et al. | |
| 2004/0247670 | A1 * | 12/2004 | Hennink et al. | 424/468 |
| 2005/0008610 | A1 | 1/2005 | Schwarz et al. | |
| 2005/0277739 | A1 | 12/2005 | Yang et al. | |
| 2006/0074186 | A1 * | 4/2006 | Barron et al. | 524/800 |
| 2006/0128918 | A1 | 6/2006 | Chu et al. | |
| 2006/0251581 | A1 | 11/2006 | McIntyre et al. | |
| 2006/0251582 | A1 * | 11/2006 | Reb | 424/9.41 |
| 2006/0251697 | A1 | 11/2006 | Li et al. | |
| 2007/0005140 | A1 * | 1/2007 | Kim et al. | 623/17.16 |
| 2008/0131512 | A1 * | 6/2008 | Hennink et al. | 424/487 |
| 2008/0260833 | A1 * | 10/2008 | Hirt et al. | 424/486 |
| 2011/0129941 | A1 * | 6/2011 | Kumacheva et al. | 436/180 |

FOREIGN PATENT DOCUMENTS

| | | |
|---|---|---|
| JP | 06-056676 A | 1/1994 |
| WO | WO 0109198 A1 * | 2/2001 |

OTHER PUBLICATIONS

Morris et al. Journal of Colloid and Interface Science 1997 190:198-205.*
Soga et al. Langmuir 2004 20:9388-9395.*
Rijcken et al. Biomacromolecules 2005 6:2343-2351.*
Gardel et al. "Microrheology." Microscale Diagnostic Techniques Ed. K. Breuer Heidelberg:Springer-Verlag, 2005. 35-37.*
Aoki et al. Macromolecules 1994 27:947-952.*
Stile et al. Biomacromolecules 2002 3:591-600.*
Neradovic et al. Macromolecules 2001 34:7589-7591.*
Cadee et al. Polymer 1999 40:6877-6881.*
Chen et al. (Polymer 2000 41:141-147.*
Yoshida et al. (Polymers for Advanced Technologies 2005 16:183-188.*
Escobar et al. (Journal of Applied Polymer Science 2004 91:3433-3437.*
Barker et al. (Macromolecules 2003 36:7765-7770.*
Nagaoka et al. (Macromolecules 1993 26:7386-7388.*
D'Emanuele et al. International Journal of Pharmaceutics 1995 118:237-242.*
Osamu Soga, "Biodegradable thermosensitive polymers: synthesis, characterization and drug delivery applications," Ph.D. thesis, Utrecht University, The Netherlands, Mar. 2006.
R. Da Silva et al., "Effect of the Crosslinking Degree on the Morphology and Swelling Ratio of PNIPAAm/AAc Hydrogels," XX Congresso da Sociedade Brasileria de Microscopia e Microanalise, Aguas de Lindoia, Brazil, Aug. 28-31, 2005.
Nicholas A. Peppas et al., "Interpenetrating Polymeric Networks," Encyclopedia of Biomaterials and Biomedical Engineering, Taylor & Francis, 2006, pp. 1-9.
Ruta Masteikova et al., "Stimuli-sensitive hydrogels in controlled and sustained drug delivery," Medicina (Kaunas), 2003, 39 Suppl. 2, pp. 19-24.
Anthony J. Convertine et al., "Direct Synthesis of Thermally Responsive DMA/NIPAM Diblock and DMA/NIPAM/DMA Triblock Copolymers via Aqueous, Room Temperature RAFT Polymerization," Macromolecules, 2006, 39(5), pp. 1724-1730.
S.Q. Liu et al., "Thermally sensitive micelles self-assembled from poly(N-isopropylacrylamide-co-N, N-dimethyacrylamide)-b-poly(D,L-lactide-co-glycolide) for controlled delivery of pacilitaxel," Molecular BioSystems, 2005, 1, pp. 158-165.
Jing Wang et al., "Self-Actuated, Thermo-Responsive Hydrogel Valves for Lab on a Chip," Biomedical Microdevices, 2005, 7(4), pp. 313-322.
Michael D. Weir et al., "Rapid Screening of the Lower Critical Solution Temperature of Injectable Hydrogels for Tissue Engineering Applications," Transactions of the 28th Annual Meeting of the Society for Biomaterials, 2002, 169.
H. Tsutsui et al., "Synthesis and Temperature-Responsive Properties of Novel Semi-interpenetrating Polymer Networks Consisting of a Poly(acrylamide) Polymer Network and Linear Poly(acrylic acid) Chains," Macromolecules, 2006, 39(6), pp. 2291-2297.

(Continued)

*Primary Examiner* — Robert A Wax
*Assistant Examiner* — Caralynne E Helm

(57) ABSTRACT

In accordance with one aspect of the invention, injectable compositions are provided, which contain temperature-sensitive hydrogel particles. The hydrogel particles may be provided in dry form, or they may be provided in hydrated form in an aqueous fluid. The temperature-sensitive hydrogel particles may have an upper critical solution temperature (UCST) below normal body temperature, they may have a lower critical solution temperature (LCST) above normal body temperature, or they may have a LCST that changes from below normal body temperature to above normal body temperature after injection into a subject.

16 Claims, No Drawings

(56) References Cited

OTHER PUBLICATIONS

Michael D. Weir et al., "Facile Synthesis of Hydroxylated Dimethacrylates for Use in Biomedical Applications," ACS Polymer Preprints, 2001, 42(2), pp. 131-132.
Patrick Theato et al., "a, w-Functionalized poly-N-isopropylacrylamides: controlling the surface activity for vesicle adsorption by temperature," Journal of Colloidal and Interface Science, 2003, 268(1), pp. 258-262.
Osamu Soga et al., "Poly(N-(2-hydroxypropyl) Methacrylamide Mono/Di Lactate): A New Class of Biodegradable Polymers with Tuneable Thermosensitivity," Biomacromolecules, 2004, 5, pp. 818-821.
Xian-Zheng Zhang et al., "Novel Biodegradable and Thermosensitive Dex-AI/PNIPAAm Hydrogel," Macromolecular Bioscience, 2003, 3(2), pp. 87-91.
Xian-Zheng Zhang et al., "Effect of the Crosslinking Level on the Properties of Temperature-Sensitive Poly(N-isopropylacrylamide) Hydrogels," Journal of Polymer Science: Part B: Polymer Physics, 2003, 41, pp. 582-593.
Fukashi Kohori et al., "Control of adriamycin cytotoxic activity using thermally responsive polymeric micelles composed of poly(N-isopropylacrylamide-, N-dimethylacrylamide)-b-poly(D,L-lactide)," Colloids and Surfaces B: Biointerfaces, 1999, 16, pp. 195-205.
Yong Qiu et al., "Environment-sensitive hydrogels for drug delivery," Advanced Drug Delivery Reviews, 2001, 53, pp. 321-339.
Osamu Soga et al., "Thermosensitive and biodegradable polymeric micelles for paclitaxel delivery," Journal of Controlled Release, 2005, 103 pp. 341-353.

\* cited by examiner

INJECTABLE HYDROGEL COMPOSITIONS

STATEMENT OF RELATED APPLICATIONS

This application claims the benefit of U.S. Provisional Patent Application Ser. No. 60/965,930, filed Aug. 23, 2007, entitled "Injectable Hydrogel Compositions", which is incorporated in its entirety by reference herein.

FIELD OF THE INVENTION

The present invention relates to injectable compositions. More particularly, the present invention relates to compositions that contain hydrogel particles that swell in vivo upon injection.

BACKGROUND OF THE INVENTION

Many clinical situations benefit from injection of particulate compositions. For example, the technique of embolization involves the therapeutic introduction of particles into the circulation to occlude vessels, for example, to either arrest or prevent hemorrhaging or to cut off blood flow to a structure or organ. Permanent or temporary occlusion of blood vessels is desirable for managing various diseases, disorders and conditions.

In a typical embolization procedure, local anesthesia is first given over a common artery. The artery is then percutaneously punctured and a catheter is inserted and fluoroscopically guided into the area of interest. An angiogram is then performed by injecting contrast agent through the catheter. An embolic agent is then deposited through the catheter. The embolic agent is chosen, for example, based on the size of the vessel to be occluded, the desired duration of occlusion, and/or the disease, disorder or condition to be treated. A follow-up angiogram is usually performed to determine the specificity and completeness of the arterial occlusion.

Various polymer-based microspheres are currently employed to embolize blood vessels. These microspheres are usually introduced to the location of the intended embolization through microcatheters. The materials that have been used commercially include polyvinyl alcohol (PVA), acetalized PVA (e.g., Contour SE™ embolic agent, Boston Scientific, Natick, Mass., USA), crosslinked acrylic hydrogels (e.g., Embospheres®, Biosphere Medical, Rockland, Mass., USA) and sodium acrylate and vinyl alcohol copolymers (Hepasphere®, Biosphere Medical; Pat. No. JP 6056676). Similar devices have been used in chemoembolization to increase the residence time of the therapeutic after delivery. In one instance, a therapeutic agent (doxorubicin) has been directly added to polyvinyl alcohol hydrogel microspheres such that it can be released locally after delivery (e.g., DC Bead™ drug delivery chemoembolization system, Biocompatibles International plc, Farnham, Surrey, UK).

It is also known to use polymer-based microspheres as augmentative materials for aesthetic improvement, including improvement of skin contour. Furthermore, polymer-based microspheres have also been used as augmentative materials in the treatment of various diseases, disorders and conditions, including urinary incontinence, vesicourethral reflux, fecal incontinence, intrinsic sphincter deficiency (ISD) and gastro-esophageal reflux disease. For instance, a common method for treating patients with urinary incontinence is via periurethral or transperineal injection of a bulking agent that contains polymer-based microspheres. In this regard, methods of injecting bulking agents commonly require the placement of a needle at a suitable treatment region, for example, periurethrally or transperineally. The bulking agent is injected into a plurality of locations, assisted by visual aids, causing the urethral lining to coapt. In some cases additional applications of bulking agent are required.

SUMMARY OF THE INVENTION

In accordance with one aspect of the invention, injectable compositions are provided, which contain temperature-sensitive hydrogel particles. The hydrogel particles may be provided in dry form, or they may be provided in hydrated in an aqueous fluid. The temperature-sensitive hydrogel particles may have an upper critical solution temperature (UCST) below normal body temperature, they may have a lower critical solution temperature (LCST) above normal body temperature, or they may have a LCST that changes from below normal body temperature to above normal body temperature after injection into a subject.

The above and other aspects of the invention are enumerated in the following paragraphs:

Aspect 1. An injectable medical composition comprising temperature sensitive hydrogel particles, the hydrogel particles having a lower critical solution temperature (LCST) that is above normal body temperature or an upper critical solution temperature (UCST) that is below normal body temperature.

Aspect 2. The injectable medical composition of Aspect 1, wherein the hydrogel particles have a UCST that is below normal body temperature.

Aspect 3. The injectable medical composition of Aspect 1, wherein the hydrogel particles comprise an acrylamide polymer or copolymer and an acrylic acid polymer or copolymer.

Aspect 4. The injectable medical composition of Aspect 1, wherein the hydrogel particles comprise a polyacrylamide gel with interpenetrating polyacrylic acid chains.

Aspect 5. The injectable medical composition of Aspect 1, wherein the hydrogel particles have an LCST that is above normal body temperature.

Aspect 6. The injectable medical composition of Aspect 5, wherein the hydrogel particles comprise N-isopropyl acrylamide homopolymer chains.

Aspect 7. The injectable medical composition of Aspect 5, wherein the hydrogel particles comprise copolymer chains that comprise N-isopropyl acrylamide polymer and an additional monomer.

Aspect 8. The injectable medical composition of Aspect 7, wherein the additional monomer is N,N-dimethylacrylamide or N-(3-dimethylaminopropyl)acrylamide.

Aspect 9. The injectable medical composition of Aspect 5, wherein the hydrogel particles comprise poly(N-isopropyl acrylamide) homopolymer chains and poly(N,N-dimethylacrylamide) homopolymer chains.

Aspect 10. The injectable medical composition of Aspect 5, wherein the hydrogel particles comprise hydrophilic polymer chains and thermosensitive polymer chains.

Aspect 11. The injectable medical composition of Aspect 10, wherein the thermosensitive polymer chains are N-isopropyl acrylamide homopolymer or copolymer chains.

Aspect 12. The injectable medical composition of Aspect 10, wherein the thermosensitive polymer chains are copolymer chains comprising N-isopropyl acrylamide and N,N-dimethylacrylamide.

Aspect 13. The injectable medical composition of Aspect 10, wherein the hydrophilic polymer chains comprises a monomer selected from ethylene oxide, acrylamide, N,N-dimethyl acrylamide, N-hydroxymethyl acrylamide, acrylic acid, methacrylic acid, hydroxyethyl methacrylate, vinyl pyrrolidone, methyl vinyl ether, and combinations thereof.

Aspect 14. The injectable medical composition of Aspect 1, wherein the hydrogel particles are suspended in an aqueous fluid.

Aspect 15. The injectable medical composition of Aspect 1, comprising spherical hydrogel particles.

Aspect 16. The injectable medical composition of Aspect 1, wherein 95 vol % of the hydrogel particles have a longest linear cross-sectional dimension between 30 μm and 5000 μm.

Aspect 17. The injectable medical composition of Aspect 1, wherein the hydrogel particles are spherical and wherein 95 vol % of the particles have a diameter between 30 μm and 5000 μm.

Aspect 18. The injectable medical composition of Aspect 1, wherein the injectable medical composition comprises a tonicity adjusting agent.

Aspect 19. The injectable medical composition of Aspect 1, wherein the injectable medical composition is disposed within a glass container or a preloaded syringe.

Aspect 20. A method of treatment comprising injecting the injectable medical composition of Aspect 14 into a subject at a temperature that is below the UCST of the hydrogel particles, the hydrogel particles having a UCST that is below normal body temperature.

Aspect 21. A method of treatment comprising injecting the injectable medical composition of Aspect 14 into a subject at a temperature that is above the LCST of the hydrogel particles, the hydrogel particles having an LCST that is above normal body temperature.

Aspect 22. An injectable medical composition comprising temperature sensitive hydrogel particles, the hydrogel particles having an ex vivo LCST that is below normal body temperature and whose LCST increases in vivo after injection into a subject from below normal body temperature to above body temperature.

Aspect 23. The injectable medical composition of Aspect 22, wherein the UCST increases after injection due to hydrolysis.

Aspect 24. The injectable medical composition of Aspect 22, wherein the hydrogel particles comprise a copolymer chain that comprises N-(2-hydroxypropyl) methacrylamide dilactate and N-isopropyl acrylamide.

Aspect 25. The injectable medical composition of Aspect 22, wherein the hydrogel particles comprise a copolymer chain that comprises N-(2-hydroxypropyl) methacrylamide dilactate, N-(2-hydroxypropyl) methacrylamide monolactate, and N-isopropylacryamide monomers.

Aspect 26. The injectable medical composition of Aspect 22, wherein the hydrogel particles comprise a block copolymer that comprises a poly(ethylene oxide) chain and a copolymer chain that comprises N-(2-hydroxypropyl) methacrylamide dilactate, N-(2-hydroxypropyl) methacrylamide monolactate, and N-isopropylacryamide monomers.

Aspect 27. The injectable medical composition of Aspect 22, wherein the hydrogel particles are suspended in an aqueous fluid.

Aspect 28. A method of treatment comprising injecting the injectable medical composition of Aspect 27 into a subject, wherein the hydrogel particles have an ex vivo LCST that is below injection temperature and below normal body temperature.

Aspect 29. A method of treatment comprising injecting the injectable medical composition of Aspect 27 into a subject, wherein the hydrogel particles have an ex vivo LCST that is above injection temperature and below normal body temperature.

These and various additional aspects, embodiments and advantages of the present invention will become immediately apparent to those of ordinary skill in the art upon review of the Detailed Description and Claims to follow.

DETAILED DESCRIPTION

Temperature-sensitive hydrogels are able to swell or shrink in aqueous fluids as a result of a change in temperature of the surrounding fluid. Negative temperature-sensitive hydrogels have a lower critical solution temperature (LCST). They contract when heated above the LCST and expand when cooled below the LCST. Positive temperature-sensitive hydrogels have an upper critical solution temperature (UCST). They contract when cooled below the UCST and expand when heated above the UCST. In the present invention, particles formed from such hydrogels are used in injectable compositions.

For example, in accordance with one aspect of the invention, injectable compositions are provided, which contain temperature-sensitive hydrogel particles (also referred to herein as "hydrogel particles" or "particles"). The hydrogel particles may be provided in dry form, or they may be provided in hydrated in an aqueous fluid. For example, the temperature-sensitive hydrogel particles may have an upper critical solution temperature (UCST) below normal body temperature, or they may have a lower critical solution temperature (LCST) above normal body temperature.

Such injectable compositions have utility, for example, in conjunction with embolic procedures, bulking procedures, procedures in which therapeutic agent is locally introduced to a subject via release from small particles, and so forth.

For instance, in some embodiments of the invention, hydrogel particles having a UCST below normal body temperature are injected into the body of a subject. Subjects include vertebrate subjects, particularly humans and various warm-blooded animals including pets and livestock. By injecting the particles into the body at a temperature that is below the UCST of the particles, the particles may be injected into the subject in a contracted state. Upon warming in the body to above the UCST, however, the particles expand, for example, increasing their embolic or bulking effect, or modulating the release of therapeutic agent from the particles.

In some embodiments, hydrogel particles having an LCST above normal body temperature are injected into the body of a subject. By injecting the particles into the body at a temperature that is above the LCST, the particles may be injected into the subject in a contracted state. However, upon cooling in the body to below the LCST, the particles expand.

The injectable particles of the invention may take on a wide variety of regular and irregular shapes. In certain embodiments, they are spherical, for example, having the form of a perfect (to the eye) sphere or having the form of a near-perfect sphere such as a prolate spheroid (a slightly elongated sphere) or an oblate spheroid (a slightly flattened sphere). The injectable particles of the invention can be of various sizes, with typical longest linear cross-sectional dimensions (e.g., for a sphere, the diameter) ranging, for example, from 150 to 250 to 500 to 750 to 1000 to 1500 to 2000 to 2500 to 5000 microns (μm).

As used herein an "aqueous fluid" (e.g., a solution, suspension, etc.) is one which contains water, typically from 50 wt % or less to 75 wt % to 90 wt % to 95 wt % to 97.5 wt % to 99 wt % or more water.

As used herein a hydrogel is a polymeric material that absorbs water in an amount that measurably changes its dimensions. For example, a hydrogel containing particle in accordance with the invention may undergo swelling in water such that its longest linear cross-sectional dimension (e.g., for a sphere, the diameter) increases by 5% or less to 10% to 15% to 20% to 25% or more. Hydrogel, as defined herein, also embraces polymeric materials that are capable of absorbing water in an amount such that the water constitutes at least 10% of the total weight of the polymeric material.

By a "polymeric material" is meant a material that contains polymers. For example, in dry form, the hydrogel particles of the invention may contain from 50 wt % or less to 75 wt % to 90 wt % to 95 wt % to 97.5 wt % to 99 wt % or more polymers, as well as other optional agents such a therapeutic agents, among others.

As used herein, "polymers" are molecules that contain multiple copies of one or more types of constitutional units, commonly referred to as monomers. The number of monomers/constitutional units within a given polymer may vary widely, ranging, for example, from 5 to 10 to 25 to 50 to 100 to 1000 to 10,000 or more constitutional units. As used herein, the term "monomers" may refer to the free monomers and those that are incorporated into polymers, with the distinction being clear from the context in which the term is used. Polymers for use in the polymeric regions of the present invention can have a variety of architectures, including cyclic, linear and branched architectures. Branched architectures include star-shaped architectures (e.g., architectures in which three or more chains emanate from a single branch point), comb architectures (e.g., architectures having a main chain and a plurality of side chains, such as graft polymers), dendritic architectures (e.g., arborescent and hyperbranched polymers), and networked architectures (e.g., crosslinked polymers), among others.

Polymers containing a single type of incorporated monomer are called homopolymers, whereas polymers containing two or more types of monomers are referred to as copolymers. The two or more types of monomers within a given copolymer may be present in any of a variety of distributions including random, statistical, gradient and periodic (e.g., alternating) distributions, among others. One particular type of copolymer is a "block copolymer," which is a copolymer that contains two or more polymer chains of different composition, which chains may be selected from homopolymer chains and copolymer chains (e.g., random, statistical, gradient or periodic copolymer chains). As used herein, a polymer "chain" is a linear assembly of monomers and may correspond to an entire polymer or to a portion of a polymer.

As noted above, in some embodiments, the temperature-sensitive hydrogel particles of the invention may have an upper critical solution temperature (UCST) below normal body temperature. For instance, such hydrogel particles may be injected into the body of a subject at a temperature that is below the UCST of the particles, such that the particles are injected into the subject in a contracted state. Upon warming in the body to above the UCST, however, the particles expand, thereby increasing, for example, their embolic or bulking effect, or modulating the release of therapeutic agent from the particles.

Examples of materials for forming such particles include polymer networks of poly(acrylic acid) (PAA) and polyacrylamide (PAAm) homopolymers or copolymers such as poly(acrylamide-co-butyl methacrylate), which are known to have positive temperature dependence of swelling. See R. Masteikova et al., *Medicina* (Kaunas), 2003, 39 Suppl. 2: 19-24, citing Y Qiu et al., *Adv. Drug Deliv. Rev.*, 2001, 53: 321-39.

As a specific example, of such a material, H. Tsutsui et al., *Macromolecules*, 2006; 39(6) pp. 2291-2297 describe semi-interpenetrating polymer network gels consisting of a polyacrylamide (PAAm) gel and linear polyacrylic acid (PAAc) chains. Using a procedure similar to Wang et al., infra, rod- and disk-shaped polyacrylamide hydrogels were formed by using acrylamide (AAm), N,N'-methylenebisacrylamide (MBA), ammonium persulfate (APS), and N,N,N',N'-tetramethylethylenediamine (TEMED). The semi-IPN gel was prepared by infiltrating PAAc chains into the PAAm hydrogels through immersion of the hydrogels in a PAAc solution. Substantial changes in dimension were reported for the resulting hydrogels between room temperature and body temperature.

The UCST of a hydrogel may be measured, for example, using cloud point measurement techniques.

Hydrogel particles may be formed, for example, by dividing a previously formed hydrogel into smaller particles, by forming the polyacrylamide hydrogel in conjunction with a water-in-oil emulsion, or by forming the particles directly, among other methods.

In other embodiments, the temperature-sensitive hydrogel particles of the invention may have a lower critical solution temperature (LCST) above normal body temperature. For instance, such hydrogel particles may be injected into the body of a subject at a temperature that is above the LCST of the particles, such that the particles are injected into the subject in a contracted state. Upon cooling in the body to below the LCST, however, the particles expand, thereby increasing, for example, their embolic or bulking effect, or modulating the release of therapeutic agent from the particles.

In many of these embodiments, the hydrogel particles comprise an N-isopropyl acrylamide polymer. In this regard, poly(N-isopropylacryamide) (PNIPAAm) is a thermosensitive polymer having a lower critical solution temperature (LCST) of around 32° C. in an aqueous solution. The LCST can be defined as the critical temperature at which a polymer undergoes a transition from a more soluble to a less soluble state when the temperature is raised. Below its LCST, PNIPAAm is very soluble in water and appears transparent. However, as its temperature is increased above its LCST, it becomes hydrophobic, reportedly from the increased interactions between the isopropyl groups, and PNIPAAm precipitates out of the aqueous solution and becomes opaque. This is sometimes referred to as the "cloud point." Cloud point measurements are commonly used to assess LCST.

Hydrogels of crosslinked PNIPAAm possess a three-dimensional network structure, which is insoluble in water but has characteristics of reversible swelling. At a temperature below the LCST, PNIPAAm hydrogels exist in a swollen state. When the environmental temperature is raised above the LCST, however, they shrink, displaying a decrease in volume.

The LCST of a hydrogel may be measured, for example, using differential scanning calorimetry (DSC), or by using shear elasticity, viscosity, or turbidimetric methods.

Hydrogels may be crosslinked via various mechanisms including physical crosslinking, chemical crosslinking, and radiation crosslinking, among other techniques.

For example, J. Wang et al., *Biomedical Microdevices*, 2005, 7(4), 313-322, describe a procedure for PNIPAAm hydrogel formation in which NIPAAm and a crosslinking agent, N,N'-methylenebisacrylamide (MBA), are dissolved in water and the solution deoxygenated. An initiator, ammonium persulfate (APS), and an accelerator, N,N,N',N'-tetramethylethylenediamine (TEMED), are then added to the oxygen-free solution. After crosslinking overnight at room temperature, the PNIPAAm gel is recovered and immersed in water to leach out non-reacted reagents. Similarly, M. D. Weir et al. "Rapid Screening of the Lower Critical Solution Temperature of Injectable Hydrogels for Tissue Engineering Applications." *Transactions of the 28th Annual Meeting of the Society for Biomaterials*, 169 (2002) describe various crosslinking agents in addition to MBA for forming PNIPAAm hydrogels using methods like that described above (polymerization/crosslinking using APS as initiator and TEMED as accelerator). These hydroxylated dimethacrylate crosslinking agents are represented by the formula,

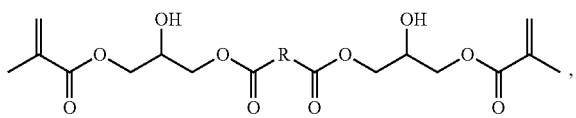

where R is

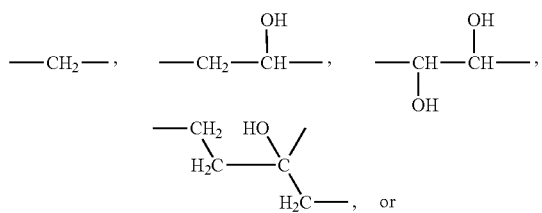

CH—(CCH—CH—)$_n$OCH—, (where n=10-12). They were formed by reacting gycidyl methacrylate with a diacid, specifically, malonic acid, L-malic acid, tartaric acid, citric acid or poly(ethylene glycol) bis(carboxymethyl) ether, respectively, using procedures described in M. D. Weir et. al., *ACS Polymer Preprints*, 2001, 42(2), 131-132. Relatively low crosslinking concentrations were employed and there was little change in the LCST (varying from 28 to 31° C.) between the various hydrogels.

Note that the final crosslinking agent can be thought of as a "macro-crosslinker" as it has a poly(ethylene glycol) chain. Other carboxyl-terminated polymer chains may be employed as macro-crosslinkers as well, particularly other carboxyl-terminated hydrophilic polymer chains, for example, carboxyl-terminated dextran, or carboxyl-terminated homopolymer and copolymer chains containing one or more hydrophilic monomers, for example, selected from ethylene oxide, acrylamide, N,N-dimethyl acrylamide, N-hydroxymethyl acrylamide, hydroxyethyl methacrylate, vinyl pyrrolidone, and methyl vinyl ether, among other hydrophilic monomers.

These and other macro-crosslinkers may be used, for example, in a polymerization/crosslinking reaction with NIPAAm and, in some instances, one or more additional monomers.

For example, US 2006/0128918 to Chu et al. describe partially biodegradable hydrogels that change in volume and shape in response to a change in pH and/or temperature. These hydrogels are prepared by UV irradiation of compositions comprising dextran-maleic acid monoester (Dex-MA) and NIPAAm. More particularly, different weight ratios of Dex-MA and NIPAAm as hydrogel precursors were dissolved in distilled water. A photoinitiator, 2,2-dimethoxy 2-phenyl acetophenone, was dissolved in N-methyl pyrrolidone (NMP), and then mixed with the aqueous solution of the hydrogel precursors. The resulting homogeneous mixture was UV-irradiated for 22 hours. Tetrahydrofuran was used to leach unreacted chemicals from the resulting gels. LCST values of 35.9, 36.5, 38.1, and 39.1° C. were reported, with the LCST increasing with increasing amounts of Dex-MA. The hydrogels disassociate over time in vivo, because the Dex-MA crosslinks are biodegradable, even though the poly(N-isopropylamide) chains are not. Similarly, X-Z Zhang et al., "Novel Biodegradable and Thermosensitive Dex-AI/PNIPAAm Hydrogel," *Macromolecular Bioscience*, 2003, 3(2), 87-91, describe the preparation of dextran-allyl isocyanate/poly(N-isopropylacrylamide) (Dex-AI/PNIPAAm) hydrogels by copolymerization of the modified dextran with NIPAAm. This resulting Dex-AI/PNIPAAm hydrogel is biodegradable and thermosensitive. The LCST was again observed to increase with an increase in dextran content.

Because the LCST of PNIPAAm is below body temperature, hydrogels used in various embodiments of the invention are formed from NIPAAm and one or more additional monomers. Copolymers of NIPAAm and various additional monomers have been reported which display an LCST above body temperature, often in conjunction with thermoreversible micelles. Several of these copolymers are described below. Hydrogels may be formed from such copolymers for example, by physical crosslinking, chemical crosslinking, radiation crosslinking, freeze/thaw, and so forth. Hydrogels may also be formed by polymerization NIPAAm, and in some cases an additional monomer, in the presence of a crosslinking agent. Crosslinking has been reported to have little effect upon LCST. For example, X.-Z. Zhang et al., "Effect of the crosslinking level on the properties of temperature-sensitive poly(N-isopropylacrylamide) hydrogels," *Journal of Polymer Science Part B: Polymer Physics*, 41(6) 2003, 582-593 report that PNIPAAm hydrogels, having a wide range of crosslinking levels, exhibited almost the same LCST values. Likewise, R. da Silva et al. "Effect of the Crosslinking Degree on the Morphology and Swelling Ratio of PNIPAAm/AAc Hydrogels," *XX Congresso da Sociedade Brasileira de Microscopia e Microanálise, Águas de Lindóia, Brazil*, 28-31 Aug. 2005, report that the LCST values for various poly(N-isopropylacryamide-co-acrylic acid) (PNIPAAm-co-AAc) hydrogel membranes were not significantly affected by the degree of cosslinking.

As an example of such a copolymer, P. Theato et al., *J Colloid Interface Sci*, 2003, 268(1): 258-62, report α,ωco-end-functionalized copolymers of NIPAAm and N-(3 dimethylaminopropyl) acrylamide. The LCST was observed to increase from 32° C. to over 37° C. to 47° C. with increasing amount of the comonomer, N-(3-dimethylaminopropyl) acrylamide.

As another example, Pub. No. US 2005/0277739 to Yang et al. reports copolymers containing a temperature-sensitive monomer (e.g., N-acroylpiperadine, N-t-butylacrylamide, N-piperidyl-methacrylamide or N-isopropylacrylamide), a hydrophilic monomer (e.g., acrylic acid, acrylamide, N,N'-dimethylacrylamide, or N-hydroxymethylacrylamide, acrylate, pyrrolidone or ethylene glycol) and, in certain embodiments, a hydrophobic monomer comprising at least one pH-sensitive moiety such as an unsaturated fatty acid (e.g., an omega-1 fatty acid, such as 4-pentenoic acid, 7-octenoic acid, 10-undecenoic acid, 15-hexadecenoic acid, or 19-ecosenoic acid). As a specific example, poly(N-isopropylacrylamide-co-N,N-dimethylacrylamide) (monomer ratio 3.75:1.25) was formed having a LCST in PBS (pH 7.4) of 39.5° C. (above normal body temperature). A non-block copolymer poly(N-isopropylacrylamide-co-N,N-dimethylacrylamide-co-10-undecenoic acid) [poly(NIPAAm-co-DMAAm-co-UA)] was reported to be both pH and temperature sensitive. For one polymer (having a NIPAAm:DMAAm:UA ratio of 3.5:1.75:0.5) the LCST values at pH 11.0, 7.4, 6.6, 6.0 and 5.5 were 43.0, 43.0, 41.0, 40.7 and 39.0° C., respectively (all well above normal body temperature). For another copolymer (having a NIPAAm:DMAAm: UA ratio of 3.75:1.25:0.5), the LCST values at pH 9.0 and 7.4 were found to be 40.5° C. and 38.5° C., respectively (above normal body temperature), while at pH 6.6 and 5.0, the LCST values were reduced to 35.5 and 35.2° C., respectively (below body temperature). The pH of tissue into which a bulking composition is typically injected is typically about the same as the pH of the bloodstream (e.g., normally about 7.4). Thus particles of such a material may be introduced into the body at a pH of about 6.6 (where the LCST value is about 35.5° C.) and at a temperature that is above the LCST, such that the particles are in a contracted state. After injection, the temperature of the composition adjusts to body temperature. Moreover, as the surrounding pH increases to the 7.4 pH of the tissue, the LCST rises above body temperature, causing the particles to expand.

As another example, S. Q. Liu et al., *Mol. BioSyst.*, 2005, 1, 158-165 describe poly(N-isopropylacrylamide-co-N,N-dimethylacrylamide)-b-poly(D,L-lactide-co-glycolide) [P(NIPAAm-co-DMAAm)-b-PLGA], which exhibited an LCST of 39.0° C. in PBS.

As yet another example, A. J. Convertine et al., *Macromolecules*, 2006, 39(5), 1724-1730, report aqueous, room temperature RAFT polymerization of NIPAAm and, subsequently, its block copolymerization utilizing a poly(N,N-dimethylacrylamide) macro-CTA. A series of thermally responsive AB diblock and ABA triblock copolymers were prepared. These polymers contained hydrophilic N,N-dimethylacrylamide (DMA) A blocks of fixed molecular weight and temperature-responsive NIPAAm B blocks of varied chain length. The block copolymers were capable of reversibly forming micelles in response to changes in solution temperature and the transition temperature was dependent on both the NIPAAm block length and the polymer architecture (diblock vs. triblock), with critical micelle temperatures (which are related to LCST), ranging between 34.6 and 44.0° C. reported.

As still another example, O. Soga et al., *Biomacromolecules* 5 (2004) 818-821 and O. Soga, "Biodegradable thermosensitive polymers: synthesis, characterization and drug delivery applications," Ph. D. Thesis, Utrecht University, The Netherlands March 2006, and references cited therein, describe various thermosensitive copolymers. For example, a random copolymer of NIPAAm with hydrophilic dimethylacrylamide (DMAAm) is reported to have a cloud point of 40° C. (citing F. Kohori et al., *Colloids Surf B: Biointerfaces* 16 (1999) 195-205). As noted above, cloud point analysis is commonly used to evaluate LCST. Poly(N-(2-hydroxypropyl)methacrylamide lactate) (poly(HPMAm-lactate) was reported to have a cloud point that can be controlled based on the length of the lactate side group (e.g. monolactate or dilactate), with values ranging between 13° C. and 65° C., depending on the ratio of HPMAm-monolactate to HPMAm-dilactate in the polymer. Values of 13° C., 25° C., 36° C., 51° C. and 65° C. were reported for molar dilactate/monolactate ratios of 100/0, 25/75, 50/50, 75/25 and 100/0, respectively. Because the ester bond of HPMAm-lactate monomer is hydrolytically sensitive, pHPMAm-dilactate is converted over time to poly(HPMAm-monolactate), and finally to the water-soluble poly(N-(2-hydroxypropyl) methacrylamide) (pHPMAm). As poly (HPMAm-dilactate) in the polymer is converted in time to poly(HPMAm-monolactate) the LCST rises. Also reported are copolymers of NIPAAm and HPMAm-lactate (poly (NIPAAm-co-HPMAm-lactate) and their block copolymers with PEG (poly(NIPAAm-co-HPMAm-lactate)-b-PEG). When 35 mol % HPMAm-lactate was copolymerized with NIPAAm, the CP of poly(NIPAAm-co-HPMAm-lactate) was around 15° C. in PBS. After hydrolysis, the CP of the hydrolyzed polymer, poly(NIPAAm-co-HPMAm), was 45° C. They found that at body temperature, the block copolymers formed polymeric micelles with a core of poly(NIPAAm-co-HPMAm-lactate) since the CP of this block is below 37° C. Due to the hydrolysis of the lactic acid side chains, the CP of the thermosensitive block increases over time, and when the CP rises above body temperature, the block polymer becomes soluble in water and the dissolution of the micelles occurs.

As noted above, by creating hydrogel particles having an LCST above body temperature, for example, from polymers such as those above among others (e.g., by crosslinking such polymers, by polymerizing such polymers in the presence of a crosslinking agent, etc.), and by injecting the particles into a subject above the LCST, the particles will have self-expanding character, thereby increasing, for example, their embolic or bulking effect, or thereby modulating the release of therapeutic agent from the particles.

In other embodiments, hydrogels may be created, for example, from polymers whose LCST rises over time in vivo after having been injected (e.g., from homopolymers and copolymers of pHPMAm-dilactate, such as those described above, among others). By selecting an LCST value for the hydrogel particles (e.g., by selecting a suitable ratio of dilactate monomer to monolactate monomer) that is both below injection temperature (e.g., room temperature) and below body temperature, such hydrogel particles may be injected into the body of a subject at a temperature where the particles are above their LCST value and are thus in a contracted state. As the LCST value of the particles rises over time to body temperature and above (such that the temperature experienced by the particles is now below their LCST value), the particles will expand. Similarly, by selecting hydrogel particles whose LCST value is below body temperature but above injection temperature, the hydrogel will initially contract upon injection, for example, providing expulsion of therapeutic agent. As the LCST rises to above body temperature, however, the hydrogel will swell, for example, providing an enhanced embolic or bulking effect, or modulation residual drug in the particles.

As indicated above, in certain embodiments, the compositions of the present invention include one or more therapeutic agents. The agents may be provided, for example, within the hydrogel particles themselves or as part of an aqueous phase within which the particles are suspended. Concentrations will vary widely depending on a number of factors including the disease, disorder or condition being treated, the potency of the therapeutic agent, and the volume of particulate composition that is ultimately injected into the subject, among other factors, and can be determined by those of ordinary skill in the art. Typical therapeutic agent concentration ranges are, for example, from about 0.1 to 50 wt % of the injected composition, more typically about 1 to 20 wt %, among other possibilities.

Examples of therapeutic agents to be used with embolic compositions include toxins (e.g., a ricin toxin, a radionuclide, or any other agent able to kill undesirable cells such as those making up cancers and other tumors such as uterine fibroids) and agents that arrest growth of undesirable cells.

Some specific examples of therapeutic agents for embolic compositions may be selected from suitable members of the following: antineoplastic/antiproliferative/anti-miotic agents including antimetabolites such as folic acid analogs/antagonists (e.g., methotrexate, etc.), purine analogs (e.g., 6-mercaptopurine, thioguanine, cladribine, which is a chlorinated purine nucleoside analog, etc.) and pyrimidine analogs (e.g., cytarabine, fluorouracil, etc.), alkaloids including taxanes (e.g., paclitaxel, docetaxel, etc.), alkylating agents such as alkyl sulfonates, nitrogen mustards (e.g., cyclophosphamide, ifosfamide, etc.), nitrosoureas, ethylenimines and methylmelamines, other aklyating agents (e.g., dacarbazine, etc.), antibiotics and analogs (e.g., daunorubicin, doxorubicin, idarubicin, mitomycin, bleomycins, plicamycin, etc.), platinum complexes (e.g., cisplatin, carboplatin, etc.), antineoplastic enzymes (e.g., asparaginase, etc.), agents affecting microtubule dynamics (e.g., vinblastine, vincristine, colchicine, Epo D, epothilone), caspase activators, proteasome inhibitors, angiogenesis inhibitors (e.g., statins such as endostatin, cerivastatin and angiostatin, squalamine, etc.), rapamycin (sirolimus) and its analogs (e.g., everolimus, tacrolimus, zotarolimus, etc.), etoposides, as well as many others (e.g., hydroxyurea, flavopiridol, procarbizine, mitoxantrone, campothecin, etc.), various pharmaceutically acceptable salts and esters of the foregoing, and combinations of the foregoing, among other agents.

Further agents suitable for treatment of uterine fibroids, many of which are suitable for the treatment of tumors other than fibroids, are listed in Pub. No. US 2006/0251581 to McIntyre et al., and include chemical ablation agents (materials whose inclusion in the formulations of the present invention in effective amounts results in necrosis or shrinkage of nearby tissue upon injection) including osmotic-stress-generating agents (e.g., salts, etc.), basic agents (e.g., sodium hydroxide, potassium hydroxide, etc.), acidic agents (e.g., acetic acid, formic acid, etc.), enzymes (e.g., collagenase, hyaluronidase, pronase, papain, etc.), free-radical generating agents (e.g., hydrogen peroxide, potassium peroxide, etc.), other oxidizing agents (e.g., sodium hypochlorite, etc.), tissue fixing agents (e.g., formaldehyde, acetaldehyde, glutaraldehyde, etc.), coagulants (e.g., gengpin, etc.), non-steroidal anti-inflammatory drugs, contraceptives (e.g., desogestrel, ethinyl estradiol, ethynodiol, ethynodiol diacetate, gestodene, lynestrenol, levonorgestrel, mestranol, medroxyprogesterone, norethindrone, norethynodrel, norgestimate, norgestrel, etc.), GnRH agonists (e.g, buserelin, cetorelix, decapeptyl, deslorelin, dioxalan derivatives, eulexin, ganirelix, gonadorelin hydrochloride, goserelin, goserelin acetate, histrelin, histrelin acetate, leuprolide, leuprolide acetate, leuprorelin, lutrelin, nafarelin, meterelin, triptorelin, etc.), antiprogestogens (e.g., mifepristone, etc.), selective progesterone receptor modulators (SPRMs) (e.g., asoprisnil, etc.), various pharmaceutically acceptable salts and esters of the foregoing, and combinations of the foregoing, among other agents.

For tissue bulking applications (e.g., urethral bulking, cosmetic bulking, etc.), specific beneficial therapeutic agents include those that promote collagen production, including proinflammatory agents and sclerosing agents such as those listed in Pub. No. US 2006/0251697 to Li et al.

Suitable proinflammatory agents can be selected, for example, from suitable endotoxins, cytokines, chemokines, prostaglandins, lipid mediators, and other mitogens. Specific examples of known proinflammatory agents from which suitable proinflammatory agents can be selected include the following: growth factors such as platelet derived growth factor (PDGF), fibroblast growth factor (FGF), transforming growth factor (such as TGF-alpha and TGF-beta), epidermal growth factor (EGF), insulinlike growth factor (IGF), interleukins such as IL-1-(alpha or beta), IL-8, IL-4, IL6, IL-10 and IL-13, tumor necrosis factor (TNF) such as TNF-alpha, interferons such as INF-gamma, macrophage inflammatory protein-2 (MIP-2), leukotrienes such as leukotriene B4 (LTB4), granulocyte macrophage-colony stimulating factor (GM-CSF), cyclooxygenase-1, cyclooxygenase-2, macrophage chemotactic protein (MCP), inducible nitric oxide synthetase, macrophage inflammatory protein, tissue factor, phosphotyrosine phosphates, N-formyl peptides such as formyl-Met-Leu-Phe (fMLP), second mitochondria-derived activator of caspase (sMAC), activated complement fragments (C5a, C3a), phorbol ester (TPA), superoxide, hydrogen peroxide, zymosan, bacterial lipopolysaccharide, chitin, imiquimod, carrageenan, various pharmaceutically acceptable salts and esters of the foregoing, and combinations of the foregoing, among other agents.

Suitable sclerosing agents for the practice of the invention can be selected, for example, from the following (which list is not necessarily exclusive of the proinflammatory list set forth above): inorganic materials such as talc, aluminum hydroxide (e.g., in slurry form), sodium hydroxide, silver nitrate and sodium chloride, as well as organic compounds, including alcohols such as ethanol (e.g., 50% to absolute), acetic acid, trifluoroacetic acid, formaldehyde, dextrose, polyethylene glycol ethers (e.g., polidocanol, also known as laureth 9, polyethylene glycol (9) monododecyl ether, and hydroxypolyethoxydodecane), tetracycline, oxytetracycline, doxycycline, bleomycin, triamcinolone, minocycline, vincristine, iophendylate, tribenoside, sodium tetradecyl sulfate, sodium morrhuate, diatrizoate meglumine, prolamine diatrizoate, alkyl cyanoacrylates such as N-butyl-2-cyano-actyalte and methyl 2-cyanoacrylate, ethanolamine, ethanolamine oleate, bacterial preparations (e.g., corynebacterium and streptococcal preparations such as picibanil) and mixtures of the same, for instance. TES (mixture of 1% tetradecyl sulfate, 32% ethanol, and 0.3% normal saline) and alcoholic solutions of zein (e.g., Ethibloc, which contains zein, alcohol, oleum papaveris, propylene glycol, and a contrast medium), and ethanol/trifluoroacetic acid mixtures, among others.

Various procedures have associated with them some degree of pain. Thus, in certain embodiments, the injectable particles of the invention contain one or more agents selected from narcotic analgesics, non-narcotic analgesics, local anesthetic agents and other pain management agents.

Examples of narcotic analgesic agents for use in the present invention may be selected from suitable members of the following: codeine, morphine, fentanyl, meperidine, propoxyphene, levorphanol, oxycodone, oxymorphone, hydromorphone, pentazocine, and methadone, among others, as well as combinations and pharmaceutically acceptable salts, esters and other derivatives of the same.

Examples of non-narcotic analgesic agents for use in the present invention may be selected from suitable members of the following: analgesic agents such as acetaminophen, and non-steroidal anti-inflammatory drugs such as aspirin, diflunisal, salsalate, ibuprofen, ketoprofen, naproxen indomethacin, celecoxib, valdecoxib, diclofenac, etodolac, fenoprofen, flurbiprofen, ketorolac, meclofenamate, meloxicam, nabumetone, naproxen, oxaprozin, piroxicam, sulindac, tolmetin, and valdecoxib, among others, as well as combinations and pharmaceutically acceptable salts, esters and other derivatives of the same.

Examples of local anesthetic agents for use in the present invention may be selected from suitable members of the following: benzocaine, cocaine, lidocaine, mepivacaine, and novacaine, among others, as well as combinations and pharmaceutically acceptable salts, esters and other derivatives of the same.

The injectable particles of the invention may be stored and transported in dry form. The dry composition may also optionally contain additional agents, for example, one or more of the following among others: (a) tonicity adjusting agents including sugars (e.g., dextrose, lactose, etc.), polyhydric alcohols (e.g., glycerol, propylene glycol, mannitol, sorbitol, etc.) and inorganic salts (e.g., potassium chloride, sodium chloride, etc.), (b) therapeutic agents, for example, selected from those listed above, (c) suspension agents including various surfactants, wetting agents, and polymers (e.g., albumen, PEO, polyvinyl alcohol, block copolymers, etc.), (d) imaging contrast agents (e.g., Omnipaque™, Visipaque™, etc.), and (e) pH adjusting agents including various buffer solutes. The dry composition may shipped, for example, in a vial, ampoule, sachette, syringe, catheter, or other container, and it may be mixed with an appropriate liquid carrier (e.g. sterile water for injection, physiological saline, phosphate buffer, a solution containing an imaging contrast agent, etc.) prior to administration. In this way the concentration of the composition to be injected may be varied at will, depending on the specific application at hand, as desired by the health care practitioner in charge of the procedure. Moreover, the composition may be protected from hydrolysis, in the event that the composition is at least partially hydrolysable as discussed above. One or more containers of liquid carrier may also be supplied in a vial or other container and shipped, along with the dry particles, in the form of a kit.

The injectable particles may also be stored in a suspension that contains water in addition to the particles themselves, as well as other optional agents such as one or more of the tonicity adjusting agents, therapeutic agents, suspension agents, contrast media, and pH adjusting agents listed above, among others. The suspension may be stored, for example, in a vial, ampoule, sachette, syringe, catheter, or other container. The suspension may also be mixed with an appropriate liquid carrier (e.g. sterile water for injection, physiological saline, phosphate buffer, a solution containing contrast agent, etc.) prior to administration, allowing the concentration of administered particles (as well as other optional agents) in the suspension to be reduced prior to injection, if so desired by the health care practitioner in charge of the procedure. One or more containers of liquid carrier may also be supplied in a vial or other container to form a kit.

The amount of injectable particles within a suspension to be injected may be determined by one skilled in the art. The amount of particles may be limited by the fact that when the amount of particles in the composition is too low, too much liquid may be injected, possibly allowing particles to stray far from the site of injection, which may result in undesired embolization or bulking of vital organs and tissues, whereas when the amount of particles is too great, the delivery device (e.g., catheter, syringe, etc.) may become clogged.

In certain embodiments, the density of the aqueous phase that suspends the particles (e.g., an injection medium that contains a saline solution that further includes a contrast agent such as Omnipaque™ or Visipaque™, among other possibilities) is close to that of the particles themselves, thereby promoting an even suspension. The density of the aqueous phase may be increased, for example, by increasing the amount of solutes that are dissolved in the aqueous phase, and vice versa.

As noted above, permanent or temporary occlusion of blood vessels is essential for managing various diseases, disorders and conditions. For example, fibroids, also known as leiomyoma, leiomyomata or fibromyoma, are the most common benign tumors of the uterus. These non-cancerous growths are present in significant fraction of women over the age of 35. In most cases, multiple fibroids are present, often up to 50 or more. Fibroids can grow, for example, within the uterine wall ("intramural" type), on the outside of the uterus ("subserosal" type), inside the uterine cavity ("submucosal" type), between the layers of broad ligament supporting the uterus ("interligamentous" type), attached to another organ ("parasitic" type), or on a mushroom-like stalk ("pedunculated" type). Fibroids may range widely in size, for example, from a few millimeters to 40 centimeters. In some women, fibroids can become enlarged and cause excessive bleeding and pain. While fibroids have been treated by surgical removal of the fibroids (myomectomy) or by removal of the uterus (hysterectomy), recent advances in uterine embolization now offer a nonsurgical treatment. Thus, injectable compositions in accordance with the present invention may be used to treat uterine fibroids.

Methods for treatment of fibroids by embolization are well known to those skilled in the art (see, e.g., Pub. No. US 2003/0206864 to Mangin and the references cited therein). Uterine embolization is aimed at starving fibroids of nutrients. Numerous branches of the uterine artery may supply uterine fibroids. In the treatment of fibroids, embolization of the entire uterine arterial distribution network is often preferred. This is because it is difficult to selectively catheterize individual vessels that supply only fibroids, the major reason being that there are too many branches for catheterization and embolization to be performed in an efficient and timely manner. Also, it is difficult to tell whether any one vessel supplies fibroids rather than normal myometrium. In many women, the fibroids of the uterus are diffuse, and embolization of the entire uterine arterial distribution affords a global treatment for every fibroid in the uterus.

In a typical procedure, a catheter is inserted near the uterine artery by the physician (e.g., with the assistance of a guide wire). Once the catheter is in place, the guide wire is removed and contrast agent is injected into the uterine artery. The patient is then subjected to fluoroscopy or X-rays. In order to create an occlusion, an embolic agent, is introduced into the uterine artery via catheter. The embolic agent is carried by the blood flow in the uterine artery to the vessels that supply the fibroid. The particles flow into these vessels and clog them, thus disrupting the blood supply to the fibroid. In order for the physician to view and follow the occlusion process, contrast agent may be injected subsequent to infusion of the embolic agent.

Controlled, selective obliteration of the blood supply to tumors is also used in treating solid tumors such as renal carcinoma, bone tumor and liver cancer, among various others. The idea behind this treatment is that preferential blood flow toward a tumor will carry embolization agent to the tumor thereby blocking the flow of blood which supplies nutrients to the tumor, thus, causing it to shrink. Embolization may be conducted as an enhancement to chemotherapy or radiation therapy.

Particle compositions in accordance with the invention may also be used to treat various other diseases, conditions and disorders, including treatment of the following: arteriovenous fistulas and malformations including, for example, aneurysms such as neurovascular and aortic aneurysms, pulmonary artery pseudoaneurysms, intracerebral arteriovenous fistula, cavernous sinus dural arteriovenous fistula and arterioportal fistula, chronic venous insufficiency, varicocele, pelvic congestion syndrome, gastrointestinal bleeding, renal bleeding, urinary bleeding, varicose bleeding, uterine hemorrhage, and severe bleeding from the nose (epistaxis), as well as preoperative embolization (to reduce the amount of bleeding during a surgical procedure) and occlusion of saphenous vein side branches in a saphenous bypass graft procedure, among other uses.

Particle compositions in accordance with the invention may also be used in tissue bulking applications, for example, as augmentative materials in the treatment of urinary incontinence, vesicourethral reflux, fecal incontinence, intrinsic sphincter deficiency (ISD) or gastro-esophageal reflux disease, or as augmentative materials for aesthetic improvement. For instance, a common method for treating patients with urinary incontinence is via periurethral or transperineal injection of a bulking material. In this regard, methods of injecting bulking agents commonly require the placement of a needle at a treatment region, for example, periurethrally or transperineally. The bulking agent is injected into a plurality of locations, assisted by visual aids, causing the urethral lining to coapt. In some cases, additional applications of bulking agent may be required.

As noted above, the injectable compositions of the invention may also be used to deliver one or more therapeutic agents locally in order to treat any of a number of diseases, disorders and conditions treatable by local drug delivery.

The precise dose of the injectable composition of the present invention to be employed will depend on the nature of the disease, disorder or condition being treated, the particular type and size of the particles used, and the mode of administration, among other factors, and should be decided according to the judgment of the practitioner and each subject's circumstances according to acceptable clinical procedure. An effective amount is, for example, (a) an amount sufficient to produce an occlusion or emboli at a desired site in the body, (b) an amount sufficient to achieve the degree of bulking desired (e.g., an amount sufficient to improve urinary incontinence, vesicourethral reflux, fecal incontinence, ISD or gastro-esophageal reflux, or an amount sufficient for aesthetic improvement), or (c) an amount sufficient to locally treat a disease, disorder or condition. Effective doses may also be extrapolated from dose-response curves derived from animal model test systems, among other techniques.

The present invention encompasses various ways of administering the particulate compositions of the invention to effect embolization, bulking or therapeutic agent release. One skilled in the art can determine the most desirable way of administering the particles depending on the type of treatment and the condition of the patient, among other factors. Methods of administration include, for example, percutaneous techniques as well as other effective routes of administration. For example, the particulate compositions of the invention may be delivered through a syringe or through a catheter, for instance, a Tracker® microcatheter (Boston Scientific, Natick, Mass., USA), which can be advanced over a guidewire, a steerable microcatheter, or a flow-directed microcatheter (MAGIC, Balt, Montomorency, France).

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. An injectable medical composition comprising temperature sensitive hydrogel particles that comprise a crosslinked polymer and a therapeutic agent, said hydrogel particles having an ex vivo lower critical solution temperature (LCST) that is below normal body temperature and whose LCST increases in vivo after injection into a subject from below normal body temperature to above body temperature, wherein 95 vol % of the hydrogel particles have a longest linear cross-sectional dimension between 30 µm and 5000 µm.

2. The injectable medical composition of claim 1, wherein the LCST increases after injection due to hydrolysis.

3. The injectable medical composition of claim 1, wherein the hydrogel particles comprise a copolymer chain that comprises N-(2-hydroxypropyl) methacrylamide dilactate and N-isopropyl acrylamide.

4. The injectable medical composition of claim 3, wherein said hydrogel particles are suspended in an aqueous fluid.

5. A method of treatment comprising injecting the injectable medical composition of claim 4 into a subject, wherein the hydrogel particles have an ex vivo LCST that is below injection temperature and below normal body temperature, wherein said method of treatment is a tissue bulking treatment or an embolization treatment.

6. The injectable medical composition of claim 1, wherein the hydrogel particles comprise a copolymer chain that comprises N-(2-hydroxypropyl) methacrylamide dilactate, N-(2-hydroxypropyl) methacrylamide monolactate, and N-isopropylacryamide monomers.

7. The injectable medical composition of claim 1, wherein the hydrogel particles comprise a block copolymer that comprises a poly(ethylene oxide) chain and a copolymer chain that comprises N-(2-hydroxypropyl) methacrylamide dilactate, N-(2-hydroxypropyl) methacrylamide monolactate, and N-isopropylacryamide monomers.

8. The injectable medical composition of claim 1, wherein said hydrogel particles are suspended in an aqueous fluid.

9. A method of treatment comprising injecting the injectable medical composition of claim 8 into a subject, wherein the hydrogel particles have an ex vivo LCST that is below injection temperature and below normal body temperature, wherein said method of treatment is a tissue bulking treatment or an embolization treatment.

10. A method of treatment comprising injecting the injectable medical composition of claim 8 into a subject, wherein the hydrogel particles have an ex vivo LCST that is above injection temperature and below normal body temperature, wherein said method of treatment is a tissue bulking treatment or an embolization treatment.

11. The injectable medical composition of claim 1, wherein the microparticles are in dry form.

12. The injectable medical composition of claim 1, wherein the injectable medical composition comprises a tonicity adjusting agent.

13. The injectable medical composition of claim 1, wherein the injectable medical composition is disposed within a glass container or a preloaded syringe.

14. The injectable composition of claim 1, wherein the therapeutic agent is selected from an antineoplastic agent, an antiproliferative agent and an antimitotic agent.

15. The injectable composition of claim 1, wherein the therapeutic agent is a radionuclide.

16. The injectable composition of claim 1, wherein the therapeutic agent is selected from narcotic analgesics, non-narcotic analgesics and local anesthetic agents.

* * * * *